United States Patent
Bess et al.

(10) Patent No.: US 12,125,568 B2
(45) Date of Patent: *Oct. 22, 2024

(54) SYSTEMS AND METHODS FOR HEALTHCARE FEES TRANSPARENCY AND COLLECTIONS AT THE TIME OF SERVICE

(71) Applicant: 4MEDICA, INC., Marina Del Rey, CA (US)

(72) Inventors: Oleg Bess, Beverly Hills, CA (US); Vannamuthu Kuttalingam, Scottsdale, AZ (US); Adam Bess, Beverly Hills, CA (US)

(73) Assignee: 4MEDICA, INC., Marina Del Rey, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/147,677

(22) Filed: Dec. 28, 2022

(65) Prior Publication Data

US 2023/0162826 A1    May 25, 2023

Related U.S. Application Data

(63) Continuation of application No. 15/896,514, filed on Feb. 14, 2018, now Pat. No. 11,568,965.

(51) Int. Cl.
*G16H 10/60*        (2018.01)
*G06Q 10/10*        (2023.01)
(Continued)

(52) U.S. Cl.
CPC .............. *G16H 10/60* (2018.01); *G06Q 10/10* (2013.01); *G06Q 20/102* (2013.01); *G16H 15/00* (2018.01); *H04W 4/12* (2013.01)

(58) Field of Classification Search
CPC ........ G16H 10/60; G16H 30/20; G16H 40/67; G16H 50/50; G16H 50/70; G16H 80/00;
(Continued)

(56) References Cited

U.S. PATENT DOCUMENTS

| 11,568,965 B2 | 1/2023 | Bess et al. | |
| 2008/0027760 A1 * | 1/2008 | Flam | G06Q 40/08 705/4 |

(Continued)

FOREIGN PATENT DOCUMENTS

| WO | WO-2006057953 A2 * | 6/2006 | ......... G06Q 10/0633 |
| WO | 2019160707 A1 | 8/2019 | |

OTHER PUBLICATIONS

Bojke, Laura et al. ; nforming Reimbursement Decisions Using Cost-Effectiveness Modelling: A Guide to the Process of Generating Elicited Priors to Capture Model Uncertainties; PharmacoEconomics 35.9: 867-877. Springer Nature B.V. (Sep. 2017) (Year: 2017).*

(Continued)

*Primary Examiner* — Hiep V Nguyen
(74) *Attorney, Agent, or Firm* — Faegre Drinker Biddle & Reath LLP

(57) ABSTRACT

An electronic healthcare system for delivering medical services is described. The electronic healthcare systems can includes modules for accessing patient electronic medical records and ordering medical services. In response to a medical service order, a cost estimation and notification module can receive information associated with the medical service order. The cost estimation and notification module can determine the patient cost responsibility and quickly notify the patient of the costs. The patient can use the determined cost information to decide whether to move forward with the ordered medical tests.

21 Claims, 8 Drawing Sheets

(51) Int. Cl.
*G06Q 20/10* (2012.01)
*G16H 15/00* (2018.01)
*H04W 4/12* (2009.01)

(58) Field of Classification Search
CPC ...... G16H 15/00; G06Q 10/00; G06Q 20/102; H04W 4/12
USPC .......................................................... 705/2
See application file for complete search history.

(56) References Cited

U.S. PATENT DOCUMENTS

| | | | | |
|---|---|---|---|---|
| 2009/0019552 | A1* | 1/2009 | McLaughlin | G16H 10/65 |
| | | | | 705/3 |
| 2013/0030828 | A1* | 1/2013 | Pourfallah | G06Q 20/384 |
| | | | | 705/2 |
| 2015/0193580 | A1* | 7/2015 | Mosier, III | G16H 40/20 |
| | | | | 705/3 |

OTHER PUBLICATIONS

U.S. Appl. No. 15/896,514, Examiner Interview Summary Record (Ptol - 413), Oct. 27, 2020, 1 pg.
U.S. Appl. No. 15/896,514, Final Rejection, Jun. 11, 2020, 26 pgs.
U.S. Appl. No. 15/896,514,- Non-Final Rejection, Nov. 25, 2019, 20 pgs.
U.S. Appl. No. 15/896,514, USPTO e-Office Action: NOA—Notice Of Allowance And Fees Due (Ptol-85), Oct. 11, 2022, 12 pages.
U.S. Appl. No. 16/206,333, Non-Final Rejection,Jun. 11, 2020, 9 pgs.
U.S. Appl. No. 15/896,514, Final Office Action mailed Jul. 30, 2021, 22 pgs.
U.S. Appl. No. 15/896,514, Non Final Office Action mailed Feb. 18, 2022, 23 pgs.
U.S. Appl. No. 15/896,514, Non-Final Office Action mailed Jan. 11, 2021, 21 pgs.
International Application No. PCT/US/2019/016634, WO2019/160707, Notice of Publication mailed Aug. 22, 2019.
International Application Serial No. PCT/US19/16634, Preliminary Report on Patentability mailed Aug. 27, 208 pgs.
Konrad, Renata Alexandra; Modeling inpatient flow from hospital information systems; Purdue University. ProQuest Dissertations Publishing, 2009. 3379423; (Year: 2009).

\* cited by examiner

Cost Estimate Interface 200

Insurer 202

Network Status 204

Co-Payment Amount 205

% co-insurance 206

Max Deductible 210

Remaining Deductible 212

| Medical Test 214 | Fee 215 | Insurance 216 | Patient 218 | Deductible 220 |
|---|---|---|---|---|
| Test 222a | Amount 224a | Amount 226a | Amount 228a | Amount 230a |
| Test 222b | Amount 224b | Amount 226b | Amount 228b | Amount 230b |

Estimated Patient Responsibility 232    Total Amount 234

Payment Interface 236

*Figure 3*

ORM-001 330

| | |
|---|---|
| MSH 302 | Fields 314 |
| NTE 334 | Fields 360 |
| PID 306 | Fields 318 |
| NTE-1 338 | Fields 364 |
| PV1 308 | Fields 320 |
| IN1 312 | Fields 324 |
| AL1 344 | Fields 370 |
| ORC 346 | Fields 372 |
| OBR 348 | Fields 374 |
| DG1 350 | Fields 376 |
| OBX 352 | Fields 378 |
| CTI 354 | Fields 380 |
| BLG 356 | Fields 382 |

*Figure 4B*

A04 Event Message 300

| | |
|---|---|
| MSH 302 | Fields 314 |
| EVN 304 | Fields 316 |
| PID 306 | Fields 318 |
| PV1 308 | Fields 320 |
| GT1 310 | Fields 322 |
| IN1 312 | Fields 324 |

*Figure 4A*

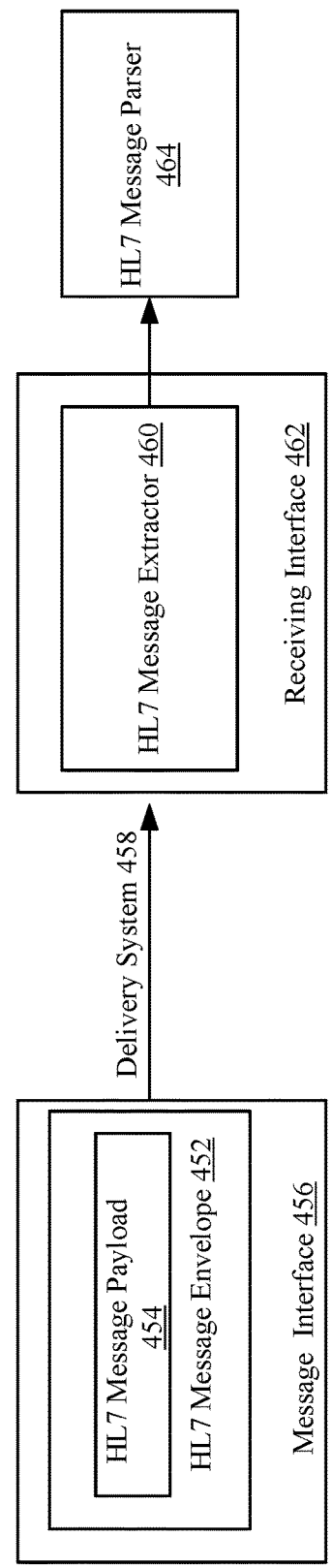

"X12-270" message 600

| | |
|---|---|
| ST 602 | Fields 628 |
| BHT 604 | Fields 630 |
| HL 606 | Fields 632 |
| NM1 608 | Fields 634 |
| HL 610 | Fields 636 |
| NM1 612 | Fields 638 |
| HL 614 | Fields 640 |
| TRN 616 | Fields 642 |
| NM1 618 | Fields 644 |
| DMG 620 | Fields 646 |
| DTP 622 | Fields 648 |
| EQ 624 | Fields 650 |
| SE 626 | Fields 652 |

*Figure 5B*

"X12-271" message 601

| | |
|---|---|
| ST 602a | Fields 628 |
| BHT 604a | Fields 630 |
| HL 606 | Fields 632 |
| NM1 608 | Fields 634 |
| HL 610 | Fields 636 |
| NM1 612 | Fields 638 |
| HL 614 | Fields 640 |
| TRN 616 | Fields 642 |
| NM1 618 | Fields 644 |
| N3 654 | Fields 664 |
| N4 656 | Fields 666 |
| DMG 658 | Fields 668 |
| DTP 660 | Fields 670 |
| EB 662 | Fields 672 |

*Figure 5C*

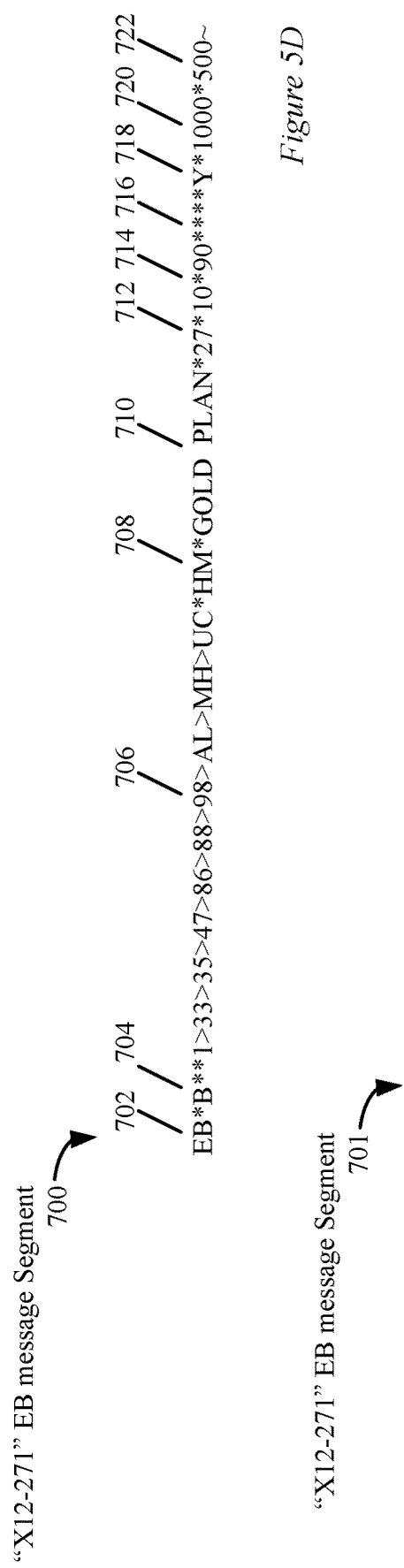

SYSTEMS AND METHODS FOR HEALTHCARE FEES TRANSPARENCY AND COLLECTIONS AT THE TIME OF SERVICE

CROSS-REFERENCE TO RELATED APPLICATIONS

The present application claims priority under 35 U.S.C. 120 to U.S. patent application Ser. No. 15/896,514, titled "SYSTEMS AND METHODS FOR HEALTHCARE FEES TRANSPARENCY AND COLLECTIONS AT THE TIME OF SERVICE," filed Feb. 14, 2018, by Bess et al. which is hereby incorporated by reference in its entirety and for all purposes.

FIELD OF THE INVENTION

This invention generally relates to delivering healthcare services and more particularly, to estimating costs associated with healthcare services at the time service is received.

BACKGROUND

Patient cost sharing has been identified as a key component to driving down the rate of healthcare inflation. For most health plans, cost sharing takes the form co-payments, deductibles and partial reimbursement of healthcare costs. The concept behind patient cost sharing is that when patients share in the costs they will make more prudent decisions in regards to utilizing their healthcare benefits.

In practice, patient cost sharing breaks down because the patient doesn't have the necessary information to make informed decisions related to healthcare costs. Typically, a patient is prescribed and receives medical services and then weeks later, is informed about their share of the costs. Thus, before receiving the prescribed treatments, the patient doesn't have the cost information necessary to make a decision on whether to receive the prescribed medical services and possibly request alternate less expensive treatments. For example, if cost information were available at the time of prescription, a patient might inquire as to whether a less expensive, but similarly effective treatment, is available.

In addition, based upon the patient cost responsibilities, the patient may simply not be able to afford a service or combination of services at a particular time. However, the patient may be able to afford a portion of the services now and then the rest later. Thus, if the cost information were available, the patient may be able to request the services be delayed or staggered in a manner that is consistent with their budget. In view of the above, new system and methods are desired which provide patients with cost sharing information earlier in the healthcare delivery process.

SUMMARY

Electronic healthcare systems are described. The electronic healthcare systems can include modules for accessing patient electronic medical records and ordering medical services. In various embodiments, a medical service ordering module can be provided to a doctor. The medical service ordering module can be executed on an electronic device accessible to the doctor.

Via the medical service ordering module, the doctor may be able to order one or more medical services, such as medical tests for a patient. In response to the medical test order, a cost estimation and notification module can receive information associated with the medical test order. The cost estimation and notification module can determine the patient cost responsibility and quickly notify the patient. The patient can use the cost information to decide whether to move forward with the ordered medical tests. In addition, the patient can request to stagger or request alternate medical tests.

In particular embodiments, an electronic healthcare system (EHS) can include one or more communication interfaces configured to communicate with electronic devices. The electronic devices, such as mobile devices and servers can be associated with medical testing services, medical practices, health insurance providers and patients. The EHS can also include a memory configured to store medical test fee information for the medical testing services and one or more processors. In one embodiment, the EHS can be instantiated in a cloud computing environment including servers with processors, memory and communication interfaces.

The one or more processors in the EHS can be configured to 1) receive, via the one or more communication interfaces, an HL7 ORM message from a first electronic device associated with a first medical practice, 2) parse the HL7 ORM message for patient information and medical test information associated with at least one order for a medical test for a patient to be fulfilled by a first medical testing service, 3) receive an HL7 ADT message from the first electronic device, 4) parse the HL7 ADT message for the patient information, patient contact information and patient insurance information, 5) based upon the patient information and the patient insurance information, generate an x12-270 message to request patient insurance benefit information, 6) send to a second electronic device, via the one or more communication interfaces, the x12-270 message, 7) receive, via the one or more communication interfaces, from the second electronic device, an x12-271 message, 8) parse the x12-271 message for the patient insurance benefit information including one or more of co-pay information, current remaining deductible, total deductible and percentage covered information, 9) based upon the patient insurance information, the order for the medical test and the first medical testing service, determine a cost of the medical test, 10) based upon the cost of the medical test and the patient insurance benefit information, determine a portion of the cost owed by the patient, 11) based upon the patient contact information and while the patient is at the first medical practice, send, via one of the communication interfaces to a third electronic device accessible by the patient, a cost notification message with a link wherein a selection of the link causes information about the medical test and the portion of the cost owed by the patient to be output to the third electronic device and 12) send, via one or more of the communication interfaces, to a fourth electronic device associated with the first medical testing service, an order message including information about the order of the medical test.

In particular embodiments, the cost notification message can be sent prior to the order of the medical test being fulfilled by the first medical testing service. Further, the x12-270 message can be generated and the portion of the cost to the patient of the medical test can be determined in response to receiving the HL7 ORM message. In some instances, the cost notification message is sent within one minute of receiving the HL7 ORM message, within five minutes of receiving the HL7 ORM message or within fifteen minutes of receiving the HL7 ORM message.

In other embodiments, the one or more processors can be further configured to send a second cost notification message to a fifth electronic device accessible to a doctor that ordered the first medical test. In addition, the one or more processors can be further configured to receive, via the one or more communication interfaces and prior to receiving the order of the medical test, a message requesting the cost of the medical test and the portion of the medical test owed by the patient. Yet further, the one or more processors can be further configured to cause a payment interface to be output to the third electronic device where the payment interface can be configured to receive information which allows the portion of the cost of the medical test to be paid to the first medical testing service.

In yet other embodiments, the medical test cost information, for each of the medical testing services can include, a) negotiated reimbursement rates and/or historical pay information for different insurance providers for a plurality of different medical tests and b) non-insurance rates for the plurality of medical tests. The processor can be further configured to receive insurance provider information. Based upon the insurance provider information and the medical test, the processor can determine a first negotiated reimbursement rate and/or first historical pay information for the medical test. Then, the processor can determine the cost of the medical test based upon the first negotiated reimbursement rate and/or the first historical pay information. In addition, the processor can be further configured to determine, based upon a first non-insurance rate and medical test, the cost of the medical test. Also, the processor can be further configured to receive, via the one or more communication interfaces, the medical test cost information from each of the medical testing services. The medical test cost information can be received in a proprietary format that varies from one medical testing service to the next medical testing service.

Another aspect of the disclosure can be related to a method in an EHS. The method can be generally characterized as including 1) receiving, via one or more communication interfaces, an HL7 ORM message from a first electronic device associated with a first medical practice, 2) parsing the HL7 ORM message for patient information and medical test information associated with at least one order for a medical test for a patient to be fulfilled by a first medical testing service, 3) receiving an HL7 ADT message from the first electronic device, 4) parsing the HL7 ADT message for the patient information, patient contact information and patient insurance information, 5) in response to receiving the HL7 ORM message and based upon the patient information and the patient insurance information, generating an x12-270 message to request patient insurance benefit information, 6) sending to a second electronic device, via the one or more communication interfaces, the x12-270 message, 7) receiving, via the one or more communication interfaces, from the second electronic device, an x12-271 message, 8) parsing the x12-271 message for the patient insurance benefit information including one or more of co-pay information, current remaining deductible, total deductible and percentage covered information, 9) based upon the patient insurance information, the order for the medical test and the first medical testing service, determining a cost of the medical test, 10) based upon the cost of the medical test and the patient insurance benefit information, determining a portion of the cost owed by the patient, 11) based upon the patient contact information, while the patient is at the first medical practice and within five minutes of receiving the HL7 ORM message, sending, via one of the communication interfaces to a third electronic device accessible by the patient, a cost notification message with a link wherein a selection of the link causes information about the medical test and the portion of the cost owed by the patient to be output to the third electronic device and 12) sending, via one or more of the communication interfaces, to a fourth electronic device associated with the first medical testing service, an order message including information about the order of the medical test.

BRIEF DESCRIPTION OF THE DRAWINGS

The included drawings are for illustrative purposes and serve only to provide examples of possible structures and process steps for the disclosed inventive systems and methods for healthcare services. These drawings in no way limit any changes in form and detail that may be made to the invention by one skilled in the art without departing from the spirit and scope of the invention.

FIG. 3 is an illustration of a patient cost estimate interface showing medical test cost estimates generated in response to a medical test order in accordance with the described embodiments.

FIG. 4A is a diagram of a HL7 ADT event message in accordance with the described embodiments.

FIG. 4B is a diagram of a HL7 ORM event message in accordance with the described embodiments.

FIG. 4C is an example of a HL7 ORM event message in accordance with the described embodiments.

FIG. 4D is a block diagram illustrating HL7 compliant message delivery in accordance with the described embodiments.

FIG. 5B is a block diagram of a x12-270 event message in accordance with the described embodiments.

FIG. 5C is a block diagram of an x12-271 event message in accordance with the described embodiments.

FIG. 5D is an example the estimated benefit portion in an x12-271 event message for in-network coverage in accordance with the described embodiments.

FIG. 5E is an example the estimated benefit portion in an x12-271 event message for out-of-network coverage in accordance with the described embodiments.

DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details.

An Electronic healthcare system (EHS) described in more detail below. The EHS can include modules for accessing patient electronic medical records and ordering medical services. In various embodiments, the EHS can be instantiated in a cloud based computing environment. One or more communication interfaces can allow the EHS to communicate with electronic devices associated with medical practices, medical testing services, insurance providers and patients.

Via a medical service ordering module instantiated on an electronic device, a doctor may be able to order one or more medical services, such as a plurality of medical tests for a patient. The EHS can be configured to receive an order message including details of the medical service order. Further, the EHS can be configured to receive patient information in the order message or in additional messages.

In response to receiving the order message, a cost estimation and notification module implemented in the EHS can be invoked and can receive information about one or more medical tests included in the order, information about an one or more medical testing services which can fulfill the one or more medical tests, information about the patient's identity, information used to contact the patient and information about the patient's insurance. Using the received information, the cost estimation and notification module can gather information necessary to perform a cost estimation for one or more medical tests included in the order, determine the patient cost responsibility and quickly notify the patient. The patient can use the determined cost information to decide whether to move forward with the ordered medical tests.

Figure 1:
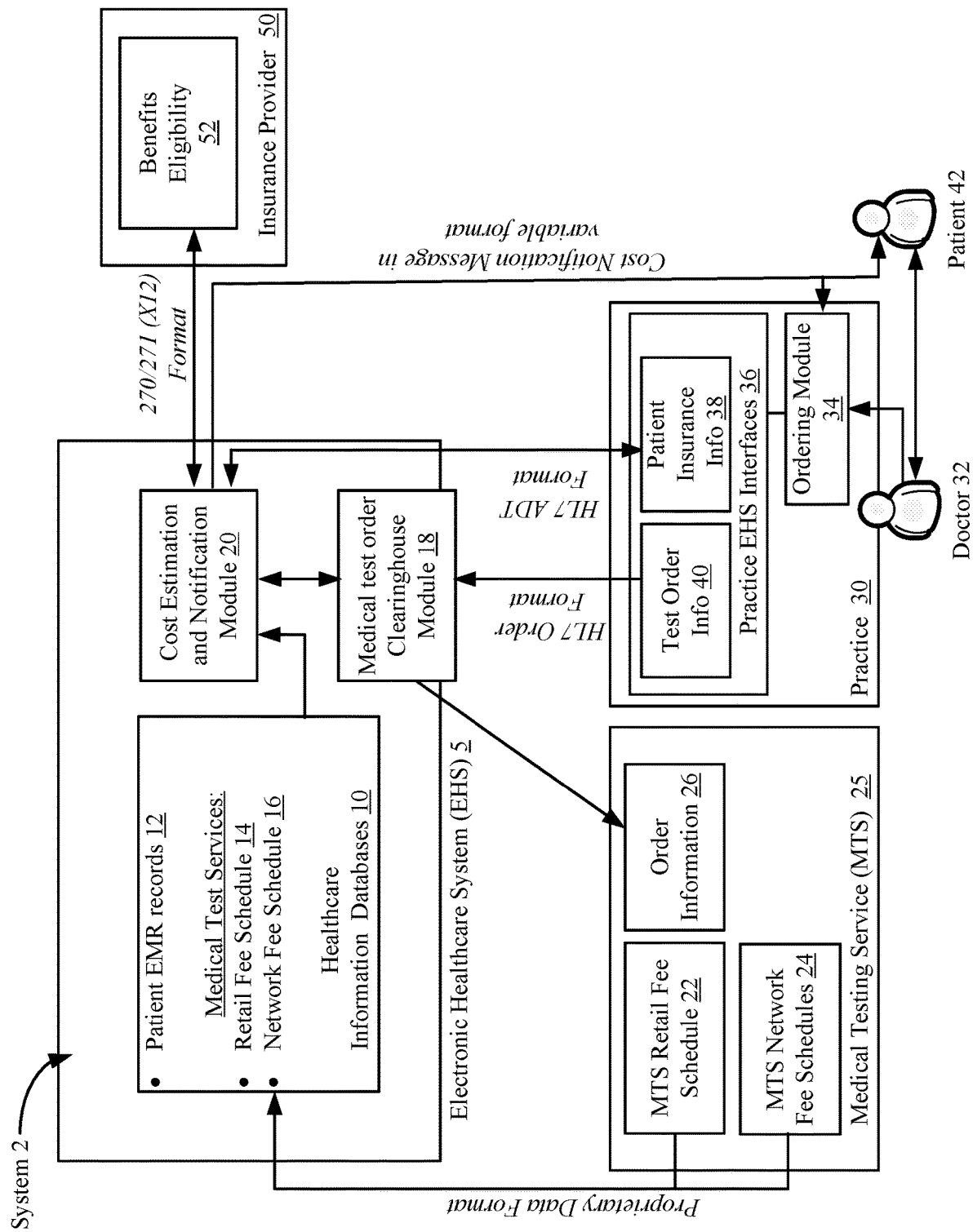
FIG. 1 is a block diagram of a system for delivering healthcare services including patient cost estimates at the time of ordering in accordance with the described embodiments.

In more detail, with respect to FIG. 1, an EHS for delivering healthcare services including cost estimates at the time of ordering is described. With respect to FIG. 2, a method for delivering healthcare services including cost estimates at the time of ordering is discussed. With respect to FIG. 3, an example of a patient cost estimate message showing lab test cost estimates generated in response to a lab test order is described.

In particular embodiments, the EHS can utilize HL7 messages to communicate medical test order and patient information, such as receive this information from a medical practice. Thus, with respect to FIGS. 4A and B, diagrams of HL7 ADT event and HL7 ORM event messages are discussed. With respect to FIG. 4C, an example of a HL7 ORM event message is described. Finally, with respect to FIG. 4D, a block diagram illustrating HL7 compliant message delivery is discussed.

In yet other embodiments, the EHS can use x12-270/271 messages to request and receive patient benefit information. The patient insurance benefit information can be used to determine the patients' cost responsibility for one or more medical tests. Thus, with respect to FIG. 5A, a block diagram illustrating x12-270/271 compliant message communications are described. With respect to FIGS. 5B and 5C block diagrams of an x12-270 event message and an x12-271 event message are described. Finally, with respect to FIGS. 5D and 5E, an example the estimated benefit portion in an x12-271 event message for in-network and out-of-network coverage are described.

Next, with respect to FIG. 1, a system overview described with respect to an example system is described. FIG. 1 is a block diagram of a system 2 for delivering healthcare services including cost estimates at the time of ordering. The system 2 can include a plurality of medical testing services (MTS), such as MTS 25, a plurality of medical practices, such as medical practice 30, a plurality of insurance providers, such as provider 50 and an electronic health care system (EHS) 5.

A patient 42 can visit a medical practice, such as practice 30, for a visit with a doctor 32. During or prior to the visit, the doctor 32 can utilize an electronic device which allows healthcare information about the patient to be accessed, such as an electronic medical record (EMR) system. In one embodiment, the EMR for the patient 42 can be managed at the EHS 5. For example, the healthcare information databases 10 can include an EMR database 12. The EMR database 12 can store an EMR for patient 42. In other embodiment, the practice 30 may include or may have access to a separate EMR system which is configured to communicate with EHS 5.

In one embodiment, via the electronic device used by the doctor, a practice EHS interface (not shown) can be used to contact the EHS 5 and retrieve an EMR for patient. As described in the previous paragraph, the EHS 5 can include an EMR system. This transaction can be an HL7 (Health Level 7) compliant communication. Additional details of an EMR system including a master patient index that can be utilized with the EHS 5 are described in co-pending U.S. patent application Ser. No. 15/605,826, filed May 25, 2017 and titled "Systems and Methods for Managing a Master Patient Index including Duplicate Record Detection," which is incorporated herein by reference in its entirety and for all purposes.

In another embodiment, the EMR for patient 42 can be stored locally on a device at the practice the 30. Thus, the electronic device utilized by the doctor 32 can be configured to retrieve information associated with an EMR for patient 42 from a local device associated with the practice. In another embodiment, the EMR can be stored on a remote device which provides an EMR system accessible to the practice. The EMR system can be separate from the ERM system associated with EHS 5. Information from the patient EMR can be output to the doctor's electronic device.

In one embodiment, the doctor's electronic device can be configured to execute an ordering module 34. The ordering module can allow the doctor 32 to access the patient's 42 EMR. The ordering module 34 can also be configured to generate an interface that allows the doctor 32 to order one or more medical tests for patient 42. The medical test order generated by the ordering module can specify a medical testing service, such as 25, which is to fulfill the medical test which has been ordered.

For example, a doctor 32 can order blood tests for the patient 42 via an electronic device. After the blood tests are ordered, the patient 42 can proceed to a phlebotomy area where blood or other specimen is collected. The phlebotomist draws the blood from the patient and places the blood in the appropriate test tubes.

The phlebotomist can also print a copy of the order, which is also called a lab requisition. In some cases, the requisition also contains "crack and peel" labels, where patient's name and bar codes are printed. These labels are placed on the test tubes.

Next, the phlebotomist can place the printed requisition into a plastic bag together with the tubes filled with blood. Each test tube can be labeled with patient's name and bar code. The bag can later be picked up by a currier and brought to the laboratory. The laboratory can be example of an MTS 25. Meanwhile, as will be described in more detail as follows, the laboratory can have received the electronic version of the requisition and can simply match them up with the specimen when it arrives.

After the order including one or more medical tests is entered via the ordering module 34, information about the order can be sent to the EHS 5. In one embodiment, to transfer information between the EHS 5 and the medical practices, such as practice 30, practice EHS interfaces 36 can be provided. A first interface can be configured to send patient insurance information 38 and/or patient demographic information. For example, the name of the insurance provider and information about the policy can be sent. The information can include demographic information, such as a name, date of birth and gender for patient 42. In addition, contact information, such as patient's mobile phone number, physical address and e-mail address can be sent via interface 38. In one embodiment, the information can be sent via and HL7 ADT (Admission Discharge Transfer) message. Details of the HL7 ADT message are described with respect to FIGS. 4A to 4D.

In another embodiment, the patient's EMR can reside at the EHS 5 in database 12. The patient's insurance information and/or demographic information can be included in database 12. Thus, the first interface in interfaces 36 may not be needed.

A second interface 40 can be provided to send the lab order information. The lab order information can provide details about the patient and details about the order, such as the type of medical test which has been ordered. The medical tests can include any type of medical tests, such as but not limited to laboratory tests, imaging tests, sonograms, electrocardiograms, hearing tests, vision tests, fitness tests, etc. In one embodiment, order information describing the medical test can be in an HL7 Order (ORM) format. Details of an HL7 format and in particular an HL7 order format are described with respect to FIGS. 4A to 4D.

At the EHS 5, n medical test clearinghouse module 18 can receive a message including the medical test order information in HL7 order format, extract a payload and parse the payload. The medical test order can include information describing one or more medical tests. The one or more medical tests can be designated to be performed by one or more different medical testing services, such as MTS 25. In response to receiving the medical test order information, the medical test order clearinghouse module 18 can generate one or more different messages to notify one or more medical testing services of the one or more medical tests which have been ordered.

For example, MTS 25 can be a laboratory, which analyzes blood and the medical test can be a blood test. The MTS 25 can be designated to perform the analysis of the blood test. Thus, the medical test order clearinghouse module 18 can send information about the ordered blood test to MTS 25, which can include one or more modules for receiving and processing the information received from module 18.

The medical test order module 18 can also pass information about the medical test order to the cost estimation and notification module 20. In one embodiment, the information can be passed to module 20 before the one or more medical testing services associated with the order are notified of the order. The module 20 can receive information needed to perform a cost estimate associated with the medical test for the patient 42. The information can include the patient's demographic information, information describing the test, the medical testing service that is to provide the test and the patient's insurance information.

In one embodiment, the patient's insurance information can be sent with the medical test order information. In another embodiment, the module 20 can be configured to request the patient's insurance information from an application executed on a device at the practice 30. For example, the module 20 can request the patient insurance information from the practice 30 via interface 38 and receive an HL7 formatted message including the insurance information (e.g., see description of FIGS. 4A and 4B). In yet another embodiment, the patient insurance information can be stored with the patient's EMR in database 12. Thus, the module 20 can retrieve the patient's insurance information from the database 12.

With the patient's insurance information, the module 20 can be configured to communicate with an electronic device at an insurance provider 50 or via an intermediary device, which can contact the insurance provider 50 to obtain the patient's current benefit information. A benefit's eligibility module 52 can be configured to receive a communication from module 20 and in response, send the patient's current benefit information.

The patient's current benefit information can include a total yearly deductible, a remaining deductible, a patient's coinsurance percentages and co-pays associated with the medical tests. In one embodiment, the communications can be performed using an "x12-270/271 message transfer" protocol. Details of this message communication protocol are described in more detail with respect to FIGS. 5A to 5E.

Next, the module 20 can gather cost information associated with each medical test included in an order. Each insurance provider (also, referred to as a payer), such as insurance provider 50, can create their own network of medical service providers. Medical service providers can include labs, doctors, practices (e.g., practice 30), hospitals, etc. Medical testing services, such as MTS 25, contract with different insurance providers. When a medical testing service, such as MTS 25, contracts with an insurance provider, the medical testing service becomes part of the insurance provider's network and are subject to the agree upon reimbursement rates negotiated with the insurance provider.

Each network can pay a different amount to the medical testing service based on the contract between that lab and the insurer. These payments can change over time as the contracts are updated or renegotiated. For example, a medical testing services' retail charge for a complete blood count (no insurance) can be twenty five dollars. The medical testing services charge for the test in a first insurance provider's network can be ten dollars. The medical testing services charge for the test in a second insurance provider's network can be twelve dollars.

In one embodiment, an EHS 5 can include an interface which allows medical testing services, such as MTS 25, to send its retail fee schedule 22 and network fee schedule 24 for different insurance providers to the EHS 5. The fee schedules can include costs associated with different medical tests provided by the medical testing service 25 as a function of the different networks. The fee schedule can include negotiated reimbursement rates between the insurance provider and the medical testing service. Typically, this information can be transferred via proprietary information format.

In another embodiment, the cost estimation and notification module 20 can be configured to handle payment information for medical testing services, such as charges from a medical testing service for medical test to a patient. Using this historical payment information, a fee schedule can be estimated for a medical testing service, such as MTS 25, for different medical tests. Thus, in some embodiments, when a particular MTS doesn't provide a fee schedule for different medical tests or when the fee schedule provided by an MTS is incomplete, historical payment information can be used to estimate a fee schedule for different medical tests as a function of the network for the MTS.

The health information database 10 can include a first database 14 which stores a retail fee schedule for a plurality of different medical testing services and a second database 16 which stores network fee schedules for a plurality of medical testing services. These databases can be populated via fee lists received from the plurality of medical testing services or built from historical payment information described in the previous paragraph. When a medical test is ordered, the medical test information, which identifies the medical test, the medical testing service information, which identifies the medical testing service associated with the medical test, and the insurance provider information, which identifies the insurance policy and provider for the patient 42, can be used to determine a cost for the medical test. Then, a cost to the patient 42 can be estimated.

For example, a patient may not have insurance. Or, the cost module may not have received insurance information. Based upon the medical test received in the order and the named medical testing service, the cost module 20 can use the retail fee schedule database 14 to determine the cost for the test for patient. For example, the cost for the medical test can be twenty five dollars. This retail cost can be the maximum cost to the patient.

In another example, the patient can have insurance. Based upon the medical test information, the medical testing service information and the insurance provider information, the cost module can locate the network fee schedule for the medical test in the network fee schedule database 16. For example, the network fee schedule for the medical test can be thirty dollars.

Based upon the network fee schedule and the patient's insurance benefit information, the portion of the cost of the medical test owed by the patient can be determined. This determination can be repeated for one or more medical tests included in the order. For example, if the patient has a coinsurance amount of 20% and the cost of the medical test is thirty dollars, then the cost to the patient can be six dollars and the cost covered by the insurance provider can be twenty four dollars.

If the patient has deductible remaining and the deductible remaining is greater than twenty four dollars then the patient's costs can be thirty dollars where twenty four of the dollars goes to the remaining deductible. If the patient has a deductible remaining and it is less than twenty four dollars, then a portion of what the patient owes can go to the fulfilling the deductible and the patient can be reimbursed for the remaining costs. For multiple medical tests in an order with a remaining deductible, the patient's cost for a first test can go toward fulfilling the deductible whereas for the second test, the deductible may have been fulfilled by the first test. In general, the total costs for a plurality of medical test in an order, which can be associated with a deductible, can be determined and then the remaining deductible can be subtracted from the total costs to determine the patient responsibility.

In particular embodiments, the patient may have a co-pay amount for a test. The co-pay amount can be addition to a co-insurance amount. The co-pay amount can be added to portion of the cost to which the patient is responsibility. For example, the cost of a medical test can be thirty dollars. The patient co-insurance amount can be ten percent with no deductible remaining. Thus, the patient cost can be three dollars. In addition, patient can have a ten dollar co-pay. Thus, the total patient cost can be thirteen dollars.

In other embodiments, the medical tests in an order can be fulfilled by multiple testing services. For example, the order can include a first medical test associated with a first medical testing service and a second medical test associated with a second medical testing service. Thus, the module 20 can be configured to determine the costs for each of the medical tests according to the fees associated with the different medical testing services specified in the order.

In yet other embodiments, the medical test can involve a medical testing service which is in network or out of network. The insurance provider can have different costs, such as different coinsurance amounts depending on whether the medical test is done in network or out of network. The cost estimation can account for whether the medical test is performed in network or out of network.

After the portion of the cost which is the patient's responsibility has been determined, the cost module can be configured to generate a cost notification message and send it to a contact mode specified by the patient. For example, the HL7 ADT message or the patient's EMR record can include an email address or a mobile phone number. In one embodiment, the cost module can be configured to generate a message, such as a text or an email that includes the patient's cost information. In some instances, the cost notification message can be sent within one minute of receiving the HL7 ORM message, within five minutes of receiving the HL7 ORM message or within fifteen minutes of receiving the HL7 ORM message.

In another embodiment, the text or the email can include a link, when the link is selected in the text or the email, a cost notification message can be displayed to an electronic device which is used to select the link, such as patient's 42 mobile device. An example of a cost notification message is described below with respect to FIG. 3.

In one embodiment, the patient costs associated with order can be sent back to the ordering module 34 used by the doctor. The ordering module 34 can be configured to then display the costs in an interface to the doctor 32. This information can allow the patient 42 and the doctor 32 to discuss the patient costs.

In one embodiment, the ordering module 34 can include a feature which allows the cost of a medical test to a patient to be determined before the medical test is ordered. For example, the ordering module 34 can allow the doctor to select a test for a cost estimate without actually ordering the test. Then, a request can be sent to the cost estimation module 20 for an estimate of the cost to the patient. This cost information can be returned to the ordering module and/or sent to the patient.

For example, after ordering a series of medical tests and receiving the cost information associated with their cost responsibility, the patient can request whether an alternate medical test can be performed which is less expensive. When an alternate medical test is available, the ordering module can be configured to allow the doctor to select the medical test for the cost estimation of the patient's costs without ordering the test. Then, the cost estimation module 20 can receive the request and return the costs the doctor 32 and/or the patient 42. In another embodiment, the doctor 32 can simply order the alternate medical test in the manner described above and the patient 42 and/or the doctor 32 can receive the cost notification message.

In various embodiments, the EHS 5 can be instantiated in a cloud computing environment. The cloud computing environment can include a plurality of processors, memories including persistent and non-persistent memories and communication interfaces. The processors, memories and communication interface can be implemented on a plurality of servers. In the cloud computing environment, one or more medical test order clearinghouse modules 18 can be instantiated at a time. Further, one or more cost estimation and notification modules 20 can be instantiated at a time. The number of modules which are instantiated at a time can depend on time varying loads, such as a number of orders which are being received per a given time period.

Figure 2:
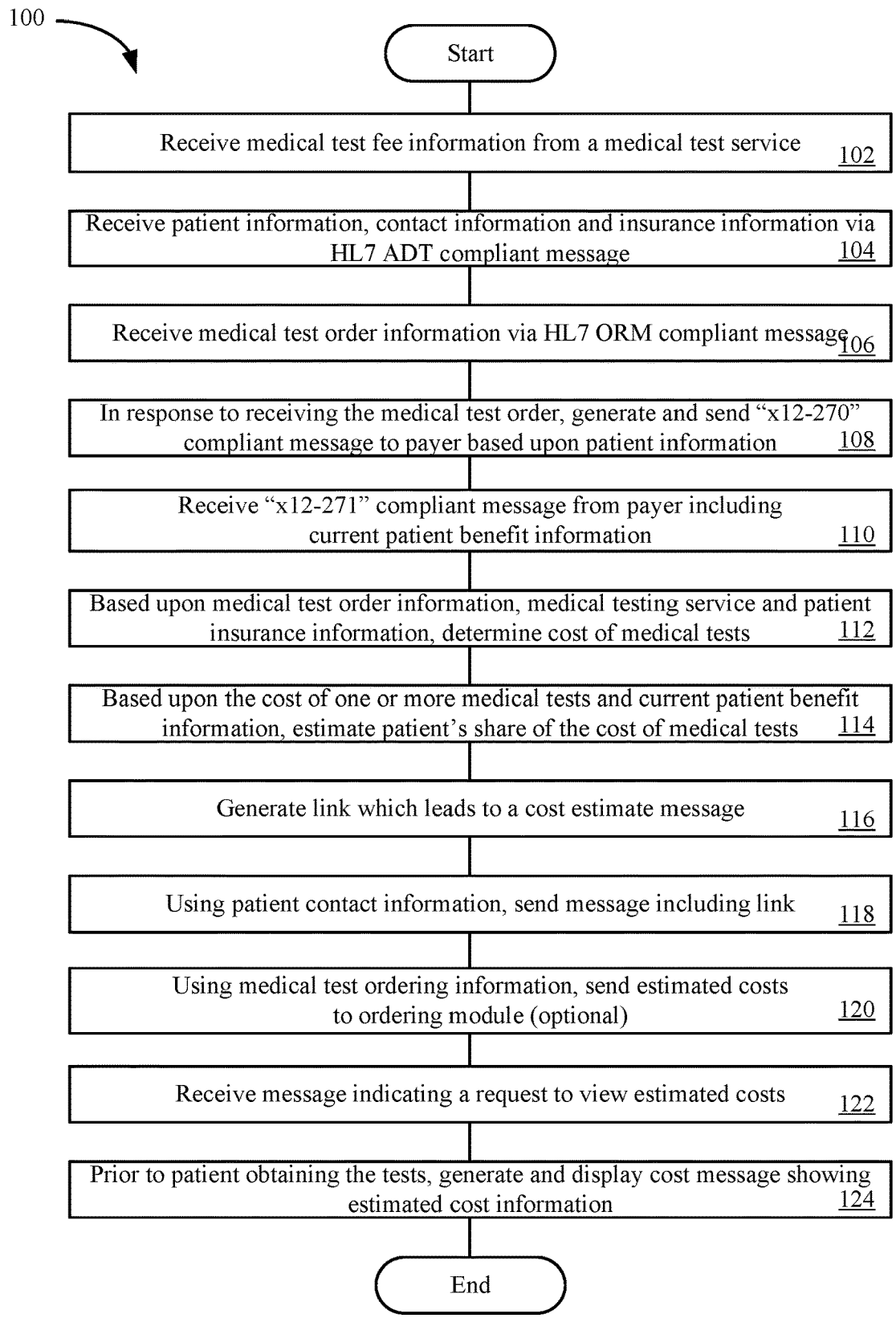
FIG. 2 is a flow chart of a method for delivering healthcare services including patient cost estimates at the time of ordering in accordance with the described embodiments.

Next, a method of determining and notifying a patient of their cost responsibility is described. FIG. 2 is a flow chart of a method 100 for delivering healthcare services including cost estimates at the time of ordering. In 102, medical test fee information can be received in an electronic healthcare system, such as EHS 5 in FIG. 1, from an electronic device at a medical testing service. As described above, the fee information can be received via a proprietary data format associated with the particular medical testing service. The fee information can include retail fees for a plurality of medical tests at non-insurance rates. In addition, the fee information can include fees for each medical test for one or more insurance providers where the fees for a particular medical test can vary from insurance provider to insurance provider.

In 104, patient information, such as patient demographic information, patient contact information and insurance information can be received via an HL7 compliant message, such as an ADT message or an ORM message. In one embodiment, the patient information can be received from an EMR system at a medical practice. In another embodiment, the EMR system can reside at the EHS 5 and all or a portion of this information can be retrieved for the patient from the local EMR system.

In 106, medical test order information describing one or more medical tests ordered for patient can be received via an HL7 ORM compliant message. For example, one or more types of blood tests to be analyzed at a laboratory can be specified in an HL7 ORM compliant message. A medical testing service, such as a laboratory or imaging service, can be specified for each of the one or medical tests. For example, a laboratory, which is to analyze a blood test, can be specified.

In response to receiving the medical test order including one or more medical tests, a patient's insurance eligibility and benefit information can be determined. In one embodiment, an "x12-270" compliant message can be generated and sent to an insurance provider (payer) or a third party insurance eligibility service, which can then contact the insurer. The "x12-270" compliant message can identify the patient and their insurance. Details of the "x12-270" transaction are described in more detail with respect to FIGS. 5A to 5E.

In response to a "x12-270" message, in 110, a "x12-271" message can be received. The "x12-271" message can include health insurance benefit information that enables a patient's portion of the cost of a medical test to be determined. The health insurance benefit information can include co-pay amounts, co-insurance percentages, a total deductible and a deductible remaining.

In 112, based upon the medical test order information included in the medical test order, a medical testing service designated to perform each of the medical tests and the patient's insurance provider information, the cost of the medical tests can be determined. In one embodiment, the cost can be determined from a fee schedule provided by the medical testing service. In another embodiment, historical reimbursement information can be used to estimate a cost of the medical test for a particular insurer provider.

In 114, based upon the cost of one or more medical tests and the current patient health insurance benefit information, a portion of the costs of the one or more medical tests to a patient can be estimated. The cost estimate can include but is not limited to a co-insurance amount owed by the patient, co-pays owed by the patient, a total deductible/remaining deductible owed by the patient and whether the service is in network or out-of-network. The cost estimate can be provided on a test by test basis and then a total cost can be generated.

Next, a patient can be notified of the cost estimate. For example, a cost notification message can be sent as a text message to mobile number provided by the patient. In another embodiment, an email can be sent to an email address provided by the patient. In one embodiment, in 116, a link, which leads to a cost estimate message can be generated. A selection of the link can cause a cost estimate interface to be generated and output to a display, such as a display on a device used to select the link. In one embodiment, cost estimate interface can be a web-interface displayed in a browser.

In 118, using the patient contact information, a message including the link can be sent to the address, such as the email address or mobile number associated with the patient contact information. In 120, in one embodiment, using the medical test ordering information, estimated patient costs for one or more medical tests can be sent to or made available for viewing on the medical test ordering module. With this information, a doctor and a patient may be able to discuss the patient costs associated with a medical test and possibly select an alternate less costly test.

In 122, a message can be received indicating a request to view estimated costs for the patient. The message can be generated in response to the activation of a link to a cost estimate in 118. In response, the cost estimate information associated with a link can be retrieved. As described above, the link can have been previously sent in a cost estimate message. In 124, prior to the patient obtaining the one or more medical tests and possibly prior to the patient leaving the practice, a cost estimate interface can be generated and displayed. The cost estimate interface can include the estimated patient costs for one or more medical tests. Further, it can include a payment interface which can allow the patient to pay their portion of the one or more medical tests.

Next, a patient cost estimate interface is described. FIG. 3 shows an example of a patient cost estimate interface 200 showing medical test cost estimates generated in response to a medical test order. The interface 200 can display a name of the insurer provider 202, an indication of whether the medical test is in network or not 204, a co-payment amount 205, a patient co-insurance percentage 206, a max deductible 210 for the patient and a remaining deductible 212. In addition, a medical testing service associated with the test can be output. If different medical testing services are utilized for different tests, then a medical testing service can be listed for each test. Further, whether medical tests are in or out of network can be specified on a test by test basis.

Then, medical tests 214, fees 215, amount paid by insurance 216, amount paid by patient 218 and deductible amount to be paid by patient 220 can be listed. In addition, co-pays for each medical test can be listed on a test by test basis.

A medical test name, such as 222a, 222b, can be listed for each test, such as blood test or urinalysis. Further, a fee amount for each test which is billed by the medical testing service, such as amount 224a and amount 224b, can be listed for each test, 222a and 222b, respectively. Also, amounts 226a and 226b, which are to be paid by insurance 216, can be listed for each test, 222a and 222b, respectively. Then, the amounts to be paid by the patient, such as 228a and 228b can be listed for each test, 222a and 222b, respectively. Finally, a deductible amount to be paid by the patient, such as 230a and 230b, which can be zero, can be listed for each test, 222a and 222b, respectively.

The total costs for all of the tests, such as the two tests, 222a and 222b, can be determined. The label "estimated patient responsibility" 232 can be output to the display. Next to the label 232, a total amount 234 can be output. The total amount is the amount the patient is expected to pay upon receiving the tests 222a and 222b. In one embodiment, the total amount the patient is expected to pay can be listed on a test by test basis. For example, the total amount the patient is expected to pay for test 222a can be listed and the total amount the patient is expected to pay for test 222b can be listed, separately. Then, a total amount can be provided.

The payment interface 236 can be used to allow the patient to pay their costs associated with one or more of the tests. For example, the payment interface can allow the patient to pay their estimated costs for test 222a, test 222b or both tests 222a and test 222b. The payments can be made prior to the patient receiving the medical tests. The payment interface can allow the patient to enter credit or debit card information or some other form of payment which allows a payment to be made.

As described above, in particular embodiments, information can be communicated using an HL7 message format. Thus, with respect to FIGS. 4A-4D aspects of HL7 message communication are described. The HL7 message communication is provided for the purposes of illustration only. Other message communications architectures can be utilized and HL7 is provided for the purposes of illustration only.

HL7 stands for Health Level-7. HL7 refers can refer to a set of standards for transfer of clinical and administrative data between software applications by various healthcare providers. Some details of the HL7 communication architecture are described below. Additional details of the HL7 communication architecture can be found at www.hl7.org (Health Level Seven International, 3300 Washtenaw Ave, Suite 227, Ann Arbor, MI).

FIG. 4A is a diagram of a HL7 ADT A04 event message 300. In one embodiment, the HL7 ADT message, such as message 300, can be used to transmit patient information. For example, patient identification information, patient contact information and patient insurance information can be sent from an electronic device at a medical practice to the electronic healthcare system (EHS) as shown in FIG. 1.

The HL7 ADT message, such as message 300, can be divided into a plurality of message segments where each message segment includes a number of fields. Different information can be specified in each field. For example, the message includes six message segments, MSH 302, EVN 304, PID 306 and PV1 308. Fields 314, 316, 318, 320, 322 and 324 are associated with each of the message segments.

The HL7 MSH (Message Header) segment 302 is usually present in every HL7 message type. It can define the message's source, purpose, destination, and certain syntax specifics like delimiters (separator characters) and character sets. The delimiters and character sets can be used to parse information from the message.

The MSH 302 fields 314 can include a field separator, encoding characters, a sending application, a sending facility, a receiving application, a receiving facility, a date/time of message, security, a message type, a message control id, a processing id, a version id, a sequence number, a continuation pointer, an accept acknowledgement type, an application acknowledgement type, a country code, a character set and a principal language of message.

The HL7 EVN (Event) type segment 304 can be used to communicate trigger event information to receiving applications. The EVN segment 304 can include seven fields. The fields 316 can include an event type code, a recorded date/time, a date/time planned event, an event reason code, an operator id and an event occurred.

The HL7 PID (patient ID) message segment 306 can be used to communicate patient demographic information. It can be found every type of ADT (Admit Discharge Transfer) message. The PID message segment 306 can include thirty fields 318. All or a portion of the fields can be specified in any message. Further, the fields which are specified can vary from message to message.

The fields 318 can include a set ID—patient ID, a patient ID (external ID), a patient ID (internal ID), an alternate Patient ID—PID, a patient name, a mother's maiden name, a date/time of birth, a sex, a patient alias, a race, a patient address, a country code, a phone number—home, a phone number—business, a primary language, a marital status, a religion, a patient account number, a SSN number—patient, a driver's license number—patient, a mother's identifier, an ethnic group, a birth place, a multiple birth indicator, a birth order, a citizenship, a veterans military status, a nationality, a patient death date and time and a patient death indicator.

In one embodiment, when the primary language is specified, a cost estimate message can be specified in the patient's primary language. The phone number field can be used to specify a mobile number which can be used to send a text message, such as a link to a cost notification message. In addition, the phone number field can be repeated and also used to specify an email address which can be used to send an email to a patient, such as a link to a cost notification message.

The PV1 (Patient Visit Information) message segment 308 can be used to specify inpatient and outpatient encounter information. It can include fifty two different fields 320. All or a portion of the fields can be specified and can vary from message to message. Some examples of the fields 320 include an assigned patient location, an admission type, an attending doctor, a referring doctor, a consulting doctor, a diet type, a servicing facility and an admit date/time.

The GT1 (Guarantor) message segment 310 can include guarantor data for patient and insurance billing applications (e.g., the person or the organization with financial responsibility for payment of a patient account). This GT1 message segment can include fifty five fields 322. All or a portion of the fields can be specified and can vary from message to message.

The fields 322 can include guarantor number, guarantor name, guarantor spouse name, guarantor address, guarantor phone number-home, guarantor phone number-business, guarantor date/time of birth, guarantor sex, guarantor type, guarantor relationship, guarantor SSN, guarantor date—begin, guarantor date—end, guarantor priority, guarantor employer name, guarantor employer address, guarantor employer phone number, guarantor employee id number, guarantor employment status, guarantor organization name, guarantor billing hold flag, guarantor credit rating code, guarantor death date and time, guarantor death flag, guarantor charge adjustment code, guarantor household annual income, guarantor household size, guarantor employer id number, guarantor marital status code, guarantor hire effective date, employment stop date, living dependency, ambulatory status, citizenship, primary language, living arrangement, publicity code, protection indicator, student indicator, religion, mother s maiden name, nationality, ethnic group, contact persons' name, contact persons' telephone number, contact reason, contact relationship, job title, job code/class, guarantor employer s organization name, handicap, job status, guarantor financial class and guarantor race.

The IN1 (insurance) message segment 312 can include insurance policy coverage information necessary to produce properly pro-rated and patient and insurance bills. The segment 312 can include forty nine fields 324. The information from this segment can be used to generate an X12-270 message, which is described below. All or a portion of the fields can be specified and can vary from message to message.

The fields 324 can include set ID—patient ID, insurance plan ID, insurance company ID, name of insured, insured's relationship to patient, insured's date of birth, insured's address, insurance company name, insurance company address, insurance co contact person, insurance co phone number, group number, plan effective date, group name, insured's group employer id, insured's group employee name, plan expiration date, authorization information, plan type, name of insured, insured's relationship to patient, insured's date of birth, insured's address, assignment of benefits, coordination of benefits, coordination of benefit priority, notice of admission flag, notice of admission date, report of eligibility flag, report of eligibility date, release information code, pre-admit certification, verification date/time, verification by, type of agreement code, billing status, lifetime reserve days, delay before lifetime reserve day, company plan code, policy number, policy deductible, policy limit—amount, policy limit—days, room rate—semi-private, room rate—private, insured's employment status, insured's sex, insured's employer's address, verification status, prior insurance plan id, coverage type, handicap and insured's ID number.

Next, an ORM event message is described. The ORM message can be used to order a number of different medical tests. As described above, the patient cost responsibility for each of the different medical tests can be determined in response to receiving an ORM message. Then, the patient can be notified of the costs, such as via a text message or email.

FIG. 4B is a diagram of a HL7 ORM-001 event message 330. The message 300 is shown with thirteen message segments including MSH 302, NTE 334, PID 306, NTE-1 338, PV1 308, AL1 344, ORC 346, OBR 348, DG1 350, OBX 352, CTI 354 and BLG 356. The message segments can be associated with fields 314, 360, 318, 364, 320, 324, 370, 372, 374, 376, 378, 380 and 382, respectively.

The NTE (Notes and comments) message segment 334 can be used to send notes and comments in a message, such as notes and comments about a medical test. It can include fields 360 such as set ID—NTE, source of comment, comment and comment type. The NTE-1 message segment 338 and fields 364 can specify additional notes and comments. The comment is limited in length. Thus, the NTE message segment can be repeated a number of times.

The AL1 (Allergy information) message segment 344 can be used to specify patient allergy information of various types. It can be repeated multiple times to specify multiple allergies. It can include six fields 370, such as set ID—AL1, allergy type, allergy code/mnemonic/description, allergy severity, allergy reaction and identification date.

The ORC (common order) message segment 346 can be used to specify can be used to transmit fields that are common to all orders (all types of services that are requested). The ORC segment can be required in the Order (ORM) message. ORC can be mandatory in Order Acknowledgment (ORR) messages if an order detail segment is present, but may not be required otherwise. The ORC segment 346 can be repeated in a message, such as to specify multiple orders of medical tests.

The ORC message segment 346 can include thirty-one fields 372. All or a portion of the fields can be specified and can vary from message to message. The filler can be the entity which fulfills a medical test described in the order. The fields 372 can include order control, placer order number, filler order number, placer group number, order status, response flag, quantity/timing parent order, date/time of transaction, entered by, verified by, ordering provider, enterer's location, call back phone number, order effective date/time, order control code reason, entering organization, entering device, action by, advanced beneficiary notice code, ordering facility name, ordering facility address, ordering facility phone number, ordering provider address, order status modifier, advanced beneficiary notice override reason, filler's expected availability date/time, confidentiality code order type, enterer authorization mode and parent universal service identifier.

The OBR message segment 348 can be used to transmit information about an exam, diagnostic study/observation, or assessment that is specific to an order or result. In an ORM message, the OBR segment 348 can be part of an optional group that provides details about the order. The OBR segment can include forty three fields 374, such as set ID—OBR, placer order number, filler order number, universal service ID, requested date/time, collection volume, collector identifier, specimen action code, relevant clinical information, specimen received date/time, ordering provider, order callback phone number, reason for study, technician scheduled date/time number of sample containers, transport logistics of collected sample, etc.

The DG1 (Diagnosis) message segment 350 can include patient diagnosis information of various types, for example, admitting, primary, etc. The DG1 segment can be used to send multiple diagnoses (for example, for medical records encoding). The DG1 message segment 350 can include nineteen fields 376, all or a portion which can be specified and vary from message to message. The fields 376 can include set ID—DG1, diagnosis coding method, diagnosis code—DG1, diagnosis description, diagnosis date/time, diagnosis type, major diagnostic category, diagnostic related group (DRG), DRG approval indicator, DRG grouper review code, outlier type outlier days, outlier cost, grouper version and type, diagnosis priority, diagnosing clinician, diagnosis classification, confidential indicator and attestation date/time.

The OBX (Observation) message segment 352 can be used to carry clinical observation/results reporting information within report messages, which are transmitted back to the requesting system, to another physician system (such as a referring physician or office practice system), or to an archival medical record system. In certain cases (such as ORM messages), the OBX segment can carry clinical information that might be needed by the receiving system to interpret the observation to be made, rather than actual information about observations and results. The OBX message segment 352 can include seventeen fields 378, all or a portion which can be specified and vary from message to message. The fields 378 can include set ID—OBX, value type observation identifier, observation sub-ID, observation value, units, reference range, abnormal flags, probability, nature of abnormal test, observation result status, data last observation normal values, user defined access checks, date/time of the observation, producer's ID, responsible observer and observation method.

The CTI (Clinical Trial Identification) message segment 354 can be an optional segment that includes information to identify the clinical trial, phase and time point with which an order or result is associated. The message segment 354 can include three fields 380. The three fields 380 can include sponsor study ID, study phase identifier and study scheduled time point.

The BLG (Billing) message segment 356 can be used to provide billing information, on the ordered service, to the filling application. As described in FIG. 1, the medical test order module 18 at the EHS 5 after receiving the ORM message can parse and then notify a filling application at the medical testing service 25. The billing information, which doesn't provide enough information to perform a cost estimation, can include three fields 382 including when to charge, charge type and account ID.

In some embodiments, the HL7 ORM message can include enough information, through the various fields, to construct a x12-270 message. Thus, it may not be necessary to obtain additional information through another source, such an HL7 ADT message or via a record request from an EMR database. As described below in more detail, the x12-270 message can be used to obtain patient insurance benefit information, which can be used to estimate a patient's share of the costs of one or more medical tests.

Next, an example of an HL7 ORM event message is described with respect to FIG. 4C. The vertical lines are used to separate fields. A space between two vertical lines indicates no value is specified for a field. The control characters 402 specify control characters used to encode the message. Different control characters can be used to parse the message and thus, can be interpreted by a message parser.

This format is provided for illustration purposes only. In other versions of HL7, XML encoding can be used (Version 3). Further, different control characters can be specified. In this example, the caret symbol can be used as a component separator in a field. The ampersand can be used as a subcomponent separator. The tilde can be used as field repeat separator. The back slash can be used as an escape character.

The sending application 404 is a healthcare application system (HIS). The sending facility 406 is a medical practice, called practice. The receiving application 408 is a laboratory information system associated with a medical testing service. The receiving facility 410 is identified as "Lab." The date and time 412 of the message is called "Date-Time." It can be a series of numbers indicating date and time the message was generated.

The message control ID 416 can be a unique identifier associated with the message. It can be a series of numbers. The version number 418 can be the version number of HL7 which was used to encode the message.

The patient ID 420 can be a unique patient identification number. It can be a combination of letters and/or numbers. The patient name 422 is referred to as "Mr. John Doe." The DOB 424 is the date of birth of the patient. The carets with no data between them refer to components which can be specified, but are unspecified. The date of birth 424 can be a series of numbers. The gender 426 can be a letter, such as M or F. The address 428 can be an address of the patient and can include numbers and letters.

The patient location 430 can be a facility where the patient is located, such as a name of a medical practice. The admission type 432 can referred to an inpatient or outpatient service. The referring doctor 434 can be a name of a doctor that referred the patient. An alternate visit ID 436 can be an additional identifier assigned to the patient visit. It can be a series of numbers and/or letters.

The order control 438 can indicate a type of order. For example, NW refers to a new order. The placer order number 440 and filler order number 442 can be numbers assigned by the placer and filler respectively to the order. The call back number 444 can be a phone number which can be used to contact the placer and get additional information about the order. In one embodiment, a cost estimation message can be sent to the call back number. The field 446 specifies information about an ordered test, which is a urinalysis.

FIG. 4D is a block diagram illustrating HL7 message delivery, which includes electronic communication between various electronic devices via a delivery system, such as the Internet. In FIG. 4D, an application (not shown) can be used to generate an HL7 message payload. For example, in FIG. 1, based upon a received order, the ordering module 34 can be configured to construct an HL7 message payload 454 which is sent to an EHS 5. FIG. 4C shows an example of an HL7 message payload for an HL7 ORM message example 400.

The message interface 456 can construct an HL7 message envelope 452. For example, the message interface 456 can be configured to embed the message payload in email with specific attributes and the send the email via the delivery system 458, such as the Internet, SFTP or HTTPS. The HL7 message can be directed to a receiving interface 462.

The receiving interface 462 can be configured to extract, using the HL7 message extractor 460, from HL7 Message envelope 452. Then, the HL7 message parser 464 can be configured to extract information from the HL7 message payload. For example, the HL7 message parser can be configured to extract insurance information and patient demographic information which can be used to construct an X12-270/271 message communication, which is described as follows.

In the following paragraphs, examples of obtaining patient insurance benefit information are described with respect to FIGS. 5A to 5E. The patient insurance benefit information can be used to determine an estimate of the patient cost responsibility for a medical test. In one embodiment, the patient insurance benefit information can be obtained using an x12-270/271 messaging protocol, which is an example of an electronic data interchange (EDI).

An x12-270 health care eligibility and benefit transaction can be used to request information from a healthcare insurance plan about a policy's coverage. The x12-270 transaction can be used in conjunction with an x12-271 transaction. The x12-271 is the health care eligibility/benefit response and is used to transmit the information requested in an x12-270.

The x12-270 transaction information can be in relation to a particular plan subscriber, which is important when individual deductibles are considered. This x12-270 transaction can be sent to insurance companies, government agencies like Medicare or Medicaid, or other organizations that would have information about a given policy. The x12-270 transaction can be used for inquiries about what services are covered for particular patients (policy subscribers or their dependents), including required copay or coinsurance.

The x12-270 transaction may be used to inquire about general information on coverage and benefits. It can also be used for questions about the coverage of specific benefits for a given plan, such as wheelchair rental, diagnostic lab services, physical therapy services, etc. Some details of x12-270/271 communication are provided as follows. Additional details are described at www.x12.org (X12, 8300 Greensboro Drive, Suite 800, Mclean, VA)

Figure 5A:
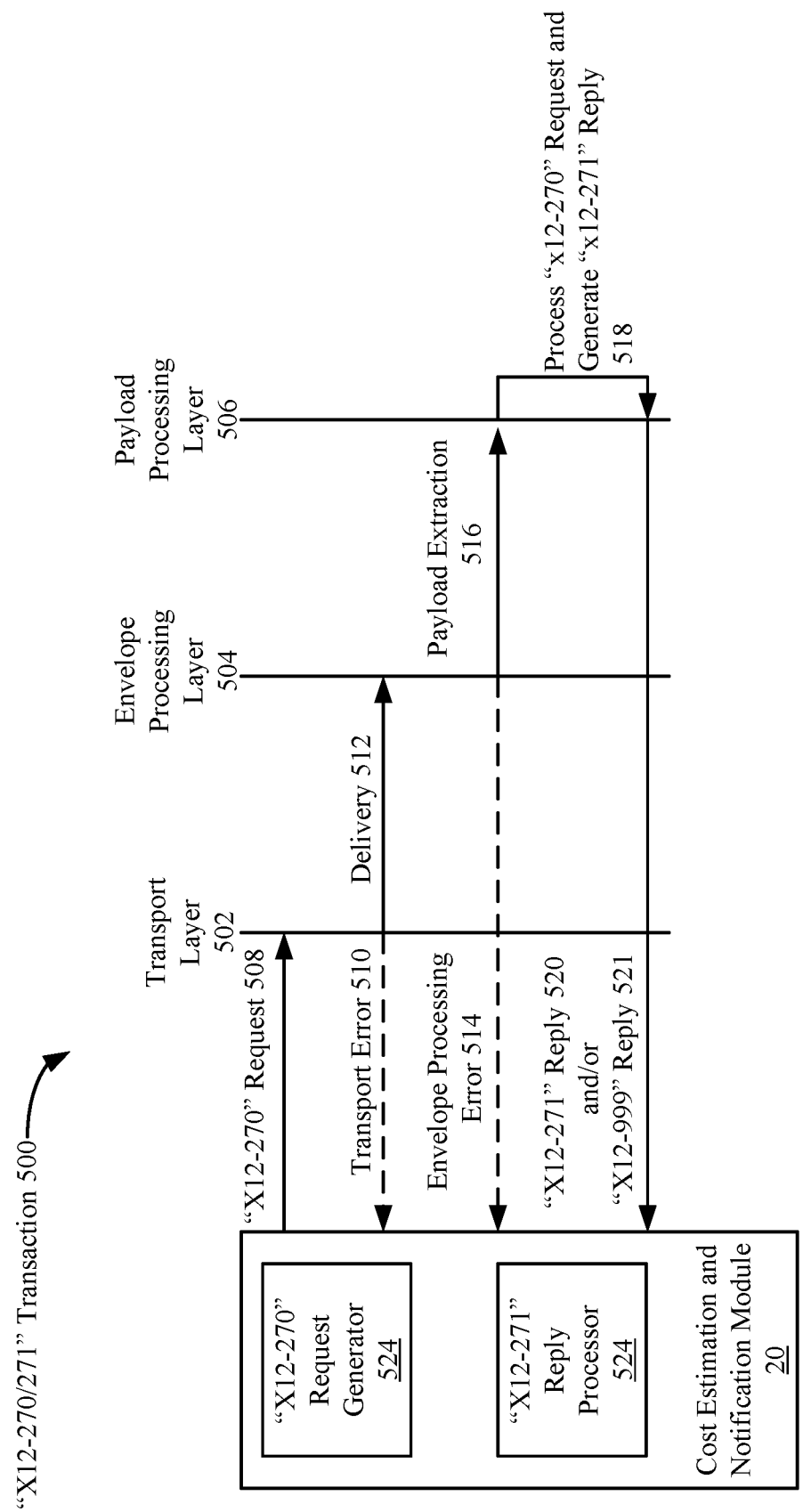
FIG. 5A is a block diagram illustrating x12-270/271 compliant message communications in accordance with the described embodiments.

FIG. 5A is a block diagram illustrating x12-270/271 compliant message communications. The cost estimation and notification module 20 (see FIG. 1) can include an "x12-270" request generator 524. The request generator 524 can be configured to generate an "x12-270" message payload and then encapsulate the payload in an envelope. Then, the generator 524 can send the "x12-270" message 508 via the transport layer 502.

For example, in one embodiment, the message payload can be encapsulated in an email, which is sent via the Internet to a recipient, such as an insurance provider. In another embodiment, the envelope can be a file which is delivered via SFTP (secure file transfer protocol). If the message 508 can't be delivered, the transport layer can send a transport error message 510, which is received by module 20. In response, the module 20 may attempt to resend the message 508 and/or generate an error flag.

In yet another example, an HTTPS or SOAP transaction can be used. Using an HTTPS or SOAP envelope, metadata such as payload type, a processing mode (batch or real-time), payload ID, encapsulation type, time stamp, username, password, sender ID, receiver ID and payload can be specified. For example, the payload can be HIPAA "x12-270" compliant.

In 512, the message can be delivered to an interface which then attempts to process the message envelope in the message envelope processing layer 504. If the envelope can't be processed. For example, if the envelope of the message 508 is in an unrecognized format. Then, the envelope processing layer 504 can generate a transport error 510 which is received by module 20.

If the envelope is recognized, then the envelope processing layer 504 can extract the payload in 516. The extracted payload can be sent to the payload processing layer 506. In 518, the payload processing layer 506 can attempt to parse the payload. If the payload can be successfully parsed, there is an error where the payload in message 508 can be only partially parsed or it can't parsed at all, this status information can be sent in a x12-999 reply message 521.

In 518, when there are no parsing errors or if there are errors but there is sufficient information, then an "x12-271" reply 520 can be generated and sent. The reply processor can process the envelope, extract the "x12-271" payload and then parse the payload for patient benefit insurance information. The patient benefit insurance information can be used to generate a portion of the cost owed by the patient.

Further, even if there are no envelope processing errors and no parsing errors, the "x12-270" request 508 may not have sufficient information to generate a response "x12-271" reply 520. As an example, to provide a proper response, a patient's first name, patient's last name, patient's date of birth and dates of eligibility requested by the provider can be required. If this information is not in the request 508, then the reply 520 may indicate that the "x12-270" response didn't include the minimum information needed to generate the "x12-271" reply.

Next details of an "x12-270" and "x12-271" messages are described with respect to FIGS. 5B and 5C. FIG. 5B is a block diagram of an x12-270 event message 600. The message can start with a number of message segments (not shown), which can be used to define envelope and parsing instructions. The first envelope can include an interchange control header (ISA) and interchange control trailer (IEA). The ISA message segment can define control characters which are utilized, such as a start as a data element separator, a colon as a sub-element separator and a tilde as segment terminator. The second envelope can include a functional group header (GS) and a functional group trailer (GE).

The third envelope can include transaction set header (ST) message segment 602 and a transaction set trailer (SE) 626 with fields 652. The transaction set header can include two fields 628. The first field can be a transaction identification code, such as "270" or "271," to indicate the type of message. The second field can be a transaction set control number, which is unique value and is repeated in the transaction set trailer.

The BHT (Beginning Hierarchical Transaction) message segment 604 can include five fields 630. The first field can be a hierarchical structure code related to the information source, information receiver, subscriber or dependent. The second field can indicate a purpose, such as a request. The remaining fields can include reference identification, which is a submitter transaction identifier returned in the "x12-271" response, a date and time when the "x12-270" transaction was created.

HL message segment 610 refers to a hierarchical ID number. It has one field 632. The NM1 message segment 608 can refer to an information source name. It can include five fields 634. The first field can be an entity identifier code, such as PR for payer. The second field can be entity type qualifier, such as a number two, which identifies a non person entity. The third field can be an organization name. The last two fields can identify the payer, such as the insurance provider.

The HL message segment 612 can be a second hierarchical ID number and can have one field 636. The second NM1 message segment 612 can be associated with a receiver of the insurance benefit. It can have three fields 638. The first field can identify the receiver, such as the medical test provider, a hospital, a facility or a gateway provider. The second field and third fields can be an identifier's such as federal tax payer identification number of national provider identifier. The TRN message segment 616 can be a trace number assigned by the insurance provider. It can have one field 642.

The next NM1 message segment 618 can be associated with the subscriber, i.e., the patient. It can have fields 644. The four fields can specify a first name, last name (or organization name), member identification number and identification code, which can be the primary subscriber ID. This information can appear on an insurance card and may have been received previously in an HL7 message.

The DMG message segment 620 can provide subscriber demographic information. The segment 620 can include two fields 646 including date time period format qualifier and a date time period. The DTP message segment 622 can include subscriber date information. It can include three fields 648. The fields 648 can be used to specify a range of dates for an eligibility determination. The EQ message segment 624 can include subscriber eligibility or benefit inquiry information. It can include a single field 650 which is a service type code, such as medical care, surgical, blood charges, anesthesia, dialysis, chemotherapy, etc.

FIG. 5C is a block diagram of an "x12-271" event message 601. The ST message segment 602a can indicate the transaction is a "271" transaction and the BHT segment 604a can indicate the message is a response. The segment 604a can also include the date and time the transaction is created. The N3 segment 654 with fields 664 and N4 segment 656 with fields 666 can be used to specify a subscriber address, city, state and zip code. The DMG segment 658 with fields 668 and DTP segment 660 with fields 670 can be used to specify subscriber demographic information and a subscriber date respectively. For example, demographic information, such as subscriber birth date, gender code, marital status, race, citizenship and country can be specified.

The EB message segment 662 with fields 672 can be used to specify an explanation of benefits. It can be used to specify whether coverage is active or not. Further, it can be used to specify information, such as benefit status, explanation of benefits, coverages, dependent coverage level, effective dates, amounts for co-insurance, co-pays, deductibles, exclusions and limitations, etc.

FIG. 5D is an example the estimated benefit portion in an X12-271 EB message segment 700 for in-network coverage. EB 702 can designate an estimated benefit message segment. The "B" 704 indicates a copayment. The field 706 includes "1>33>35>47>86>88>98>AL>MH>UC," This field indicates the benefit information is for medical care, chiropractic, dental care, hospital, emergency services, pharmacy, physician office visit, vision, mental health and urgent care.

The insurance code 708, which is HM, indicates the plan is an HMO. A plan coverage description 710 indicates it is a gold plan. The time period qualifier 712 has a value of "27," which indicates it is for a visit. The monetary value 714 is a co-pay amount, which is ten dollars. The percent field 716 indicates a percentage covered by the insurance or can be used to indicate a patient coinsurance amount, which is ninety percent in this example. The response code 718 indicated by the symbol "Y" is to indicate the service is in-network. The fields 720 and 722 are used to indicate a total deductible amount and a remaining deductible amount, which one thousand and five hundred in this example.

FIG. 5E is an example the estimated benefit portion in an x12-271 event message for out-of-network coverage. The field 728 with the symbol "N" indicates the coverage is out of network. For out of network coverage, field 724 indicates the copayment amount is 30 and the percentage covered by the insurer is fifty percent.

Embodiments of the present invention further relate to computer readable media that include executable program instructions. The media and program instructions may be those specially designed and constructed for the purposes of the present invention, or any kind well known and available to those having skill in the computer software arts. When executed by a processor, these program instructions are suitable to implement any of the methods and techniques, and components thereof, described above. Examples of computer-readable media include, but are not limited to, magnetic media such as hard disks, semiconductor memory, optical media such as CD-ROM disks; magneto-optical media such as optical disks; and hardware devices that are specially configured to store program instructions, such as read-only memory devices (ROM), flash memory devices, EEPROMs, EPROMs, etc. and random access memory (RAM). Examples of program instructions include both machine code, such as produced by a compiler, and files containing higher-level code that may be executed by the computer using an interpreter. The media including the executable program instructions can be executed on servers or other computation devices including processors and memory.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. It will be apparent to one of ordinary skill in the art that many modifications and variations are possible in view of the above teachings.

While the embodiments have been described in terms of several particular embodiments, there are alterations, permutations, and equivalents, which fall within the scope of these general concepts. It should also be noted that there are many alternative ways of implementing the methods and apparatuses of the present embodiments. It is therefore intended that the following appended claims be interpreted as including all such alterations, permutations, and equivalents as fall within the true spirit and scope of the described embodiments.

What is claimed is:

1. An electronic healthcare system comprising:
   one or more communication interfaces configured to communicate with electronic devices associated with medical testing services, medical practices, health insurance providers and patients;
   a memory configured to store medical test cost information for the medical testing services;
   one or more processors configured to 1) receive, via the one or more communication interfaces, an order format message from a first electronic device associated with a first medical practice, the order format message comprising a first configuration of data segments and fields, 2) parse the order format message for patient information and medical test information associated with at least one order for a medical test for a patient to be fulfilled by a first medical testing service, 3) receive an event message from the first electronic device, the event message comprising a second configuration of data segments and fields, 4) parse the event message for the patient information, patient contact information and patient insurance information, 5) using the patient information and the patient insurance information, generate a compliant message to request patient insurance benefit information, the compliant message comprising a third configuration of data segments and fields, 6) send to a second electronic device, via the one or more communication interfaces, the compliant message, 7) receive, via the one or more communication interfaces, from the second electronic device, a response message, the response compliant message comprising a fourth configuration of data segments and fields, 8) parse the response message for the patient insurance benefit information including one or more of co-pay information, current remaining deductible, total deductible and percentage covered information, 9) using the patient insurance information, the order for the medical test and the first medical testing service, determine a cost of the medical test, and 10) using the cost of the medical test and the patient insurance benefit information, determine a portion of the cost owed by the patient,
   wherein the order format message is a first HL7 message type, wherein the event message is a second HL7 message type, wherein the compliant message is a first x12 message type, wherein the response message is a second x12 message type.

2. The electronic healthcare system of claim 1, wherein the one or more processors is further configured to: 11) using the patient contact information and while the patient is at the first medical practice, generate and send, via one of the communication interfaces to a third electronic device accessible by the patient, a cost notification message with a link wherein a selection of the link causes information about the medical test and the portion of the cost owed by the patient to be output to the third electronic device and 12) send, via one or more of the communication interfaces, to a fourth electronic device associated with the first medical testing service, an order message including information about the order of the medical test.

3. The electronic healthcare system of claim 2, wherein the cost notification message is sent prior to the order of the medical test being fulfilled by the first medical testing service.

4. The electronic healthcare system of claim 2, wherein the compliant message is generated and the portion of the cost to the patient of the medical test is determined in response to receiving the order format message.

5. The electronic healthcare system of claim 2, wherein the cost notification message is sent within five minutes of receiving the order format message.

6. The electronic healthcare system of claim 2, wherein the order format message is an ORM message, the event message is an ADT message, the compliant message is a 12-270 message, and the response message is a 12-271 message.

7. The electronic healthcare system of claim 2 wherein the one or more processors are further configured to send a second cost notification message to a fifth electronic device accessible to a doctor that ordered the first medical test.

8. The electronic healthcare system of claim 2, wherein the one or more processors are further configured to receive, via the one or more communication interfaces and prior to receiving the order of the medical test, a message requesting the cost of the medical test and the portion of the medical test owed by the patient.

9. The electronic healthcare system of claim 8, sending the cost of the medical test and the portion of the medical test owed by the patient to a fifth electronic device accessible by a doctor or the third electronic device associated with the patient.

10. The electronic healthcare system of claim 2, wherein the one or more processors are further configured to cause a payment interface to be output to the third electronic device wherein the payment interface is configured to receive information which allows the portion of the cost of the medical test to be paid to the first medical testing service.

11. The electronic healthcare system of claim 2, wherein the medical test cost information, for each of the medical testing services includes, a) negotiated reimbursement rates and/or historical pay information for different insurance providers for a plurality of different medical tests and b) non-insurance rates for the plurality of medical tests.

12. The electronic healthcare system of claim 11, wherein the processor is further configured to receive insurance provider information and using the insurance provider information and the medical test, determine a first negotiated reimbursement rate and/or first historical pay information for the medical test and determine the cost of the medical test using the first negotiated reimbursement rate and/or the first historical pay information.

13. The electronic healthcare system of claim 11, wherein the processor is further configured to determine, using a first non-insurance rate and medical test, the cost of the medical test.

14. The electronic healthcare system of claim 11, wherein the processor is further configured to receive, via the one or more communication interfaces, the medical test cost information from each of the medical testing services.

15. The electronic healthcare system of claim 2, wherein the patient contact information includes one of an e-mail address or a phone number.

16. The electronic healthcare system of claim 15, wherein the one or more processors are configured to send the cost notification message as an e-mail message to the e-mail address or as a text message to the phone number.

17. The electronic healthcare system of claim 2, wherein the order format message includes orders for a plurality of medical tests and wherein the one or more processors is further configured to determine costs for each of the plurality of medical tests.

18. The electronic healthcare system of claim 2, wherein the order format message includes patient insurance information and patient contact information.

19. A method in an electronic healthcare system comprising:
1) Receiving, via one or more communication interfaces, an order format message from a first electronic device associated with a first medical practice, the order format message comprising a first configuration of data segments and fields, 2) parsing, in one or more processors, the order format message for patient information and medical test information associated with at least one order for a medical test for a patient to be fulfilled by a first medical testing service, 3) receiving an event message from the first electronic device, the event message comprising a second configuration of data segments and fields, 4) parsing the event message for the patient information, patient contact information and patient insurance information, 5) in response to receiving the order format message and using the patient information and the patient insurance information, generating an compliant message to request patient insurance benefit information, the compliant comprising a third configuration of data segments and fields, 6) sending to a second electronic device, via the one or more communication interfaces, the compliant message, 7) receiving, via the one or more communication interfaces, from the second electronic device, a response message, the response compliant message comprising a fourth configuration of data segments and fields, 8) parsing the response message for the patient insurance benefit information including one or more of co-pay information, current remaining deductible, total deductible and percentage covered information, 9) using the patient insurance information, the order for the medical test and the first medical testing service, determining a cost of the medical test, 10) using the cost of the medical test and the patient insurance benefit information, determining a portion of the cost owed by the patient,
wherein the order format message is a first HL7 message type, wherein the event message is a second HL7 message type, wherein the compliant message is a first x12 message type, wherein the response message is a second x12 message type.

20. The method of claim 19 further comprising: 11) using the patient contact information, while the patient is at the first medical practice and within five minutes of receiving the order format message, generating and sending, via one of the communication interfaces to a third electronic device accessible by the patient, a cost notification message with a link wherein a selection of the link causes information about the medical test and the portion of the cost owed by the patient to be output to the third electronic device and 12) sending, via one or more of the communication interfaces, to a fourth electronic device associated with the first medical testing service, an order message including information about the order of the medical test.

21. The method of claim 20, wherein the order format message includes medical test information associated with a plurality of medical tests and wherein the one or more processors is configured to determine the costs associated with each of the plurality of medical tests and determine the portion of the costs owed by the patient for each of the plurality of medical tests.

\* \* \* \* \*